United States Patent [19]

Odernheimer et al.

[11] 4,433,982
[45] Feb. 28, 1984

[54] INPUT HEAD OF A MEASURING OR IDENTIFICATION SYSTEM FOR CHEMICAL AGENTS

[75] Inventors: Bernhard Odernheimer; Johannes H. Kremer; Klaus O. Kranich, all of Munster, Fed. Rep. of Germany

[73] Assignee: Bruker-Franzen Analytik GmbH, Bremen, Fed. Rep. of Germany

[21] Appl. No.: 320,959

[22] PCT Filed: Mar. 10, 1981

[86] PCT No.: PCT/DE81/00043
§ 371 Date: Nov. 5, 1981
§ 102(e) Date: Nov. 5, 1981

[87] PCT Pub. No.: WO81/02632
PCT Pub. Date: Sep. 17, 1981

[30] Foreign Application Priority Data

Mar. 10, 1980 [DE] Fed. Rep. of Germany ....... 3009069

[51] Int. Cl.³ ............................................. B01D 53/22
[52] U.S. Cl. ....................................... 55/158; 55/197; 55/208; 55/386; 73/19
[58] Field of Search ............... 55/16, 67, 158, 197, 55/386, 208; 73/19

[56] References Cited

U.S. PATENT DOCUMENTS

| | | | |
|---|---|---|---|
| 1,174,631 | 3/1916 | Snelling | 55/158 |
| 2,671,337 | 3/1954 | Hulsberg | 55/158 X |
| 2,862,575 | 12/1958 | Birdwhistell | 55/16 |
| 3,178,864 | 4/1965 | Anderson et al. | 55/158 X |
| 3,568,411 | 3/1971 | Dravnieks et al. | 55/208 |
| 3,611,676 | 10/1971 | Christen et al. | 55/16 |
| 3,616,607 | 11/1971 | Klass et al. | 55/16 |
| 3,620,844 | 11/1971 | Wicke et al. | 55/158 X |
| 3,649,199 | 3/1972 | Littlejohn | 55/16 X |
| 3,699,342 | 10/1972 | Jenkins et al. | 55/16 X |
| 3,862,576 | 1/1975 | Pogorski | 55/16 X |
| 3,871,228 | 3/1975 | Weiss | 55/158 X |
| 3,923,461 | 12/1975 | Barden | 55/16 X |
| 3,926,561 | 12/1975 | Lucero | 55/16 X |
| 4,257,257 | 3/1981 | Dairaku et al. | 55/158 X |
| 4,293,316 | 10/1981 | Block | 55/16 |

FOREIGN PATENT DOCUMENTS

| | | |
|---|---|---|
| 1673239 | 9/1970 | Fed. Rep. of Germany . |
| 2022958 | 12/1970 | Fed. Rep. of Germany . |
| 2310264 | 9/1973 | Fed. Rep. of Germany . |
| 1573147 | 7/1969 | France . |

*Primary Examiner*—Robert H. Spitzer
*Attorney, Agent, or Firm*—Parmelee, Bollinger & Bramblett

[57] ABSTRACT

An input head for an active system for identifying and detecting chemical agents has a heated membrane directly exposed to a solid surface containing the agents to be detected. The chemical agents diffuse and traverse through the membrane and exit the rear membrane surface in a vaporized state. The membrane can be successively rinsed with a gas or used as a contact membrane as a first stage of a membrane separator acting as a direct admission system in a mass spectrometer. The input head provides a detection probe or sample admission system in which organic compounds that are likely to diffuse can be qualitatively and quantitatively detected in a sensitive and rapid procedure. The membrane of the input head is relatively thin but mechanically stable so that it may be brought into direct contact with contaminated solid surfaces.

22 Claims, 3 Drawing Figures

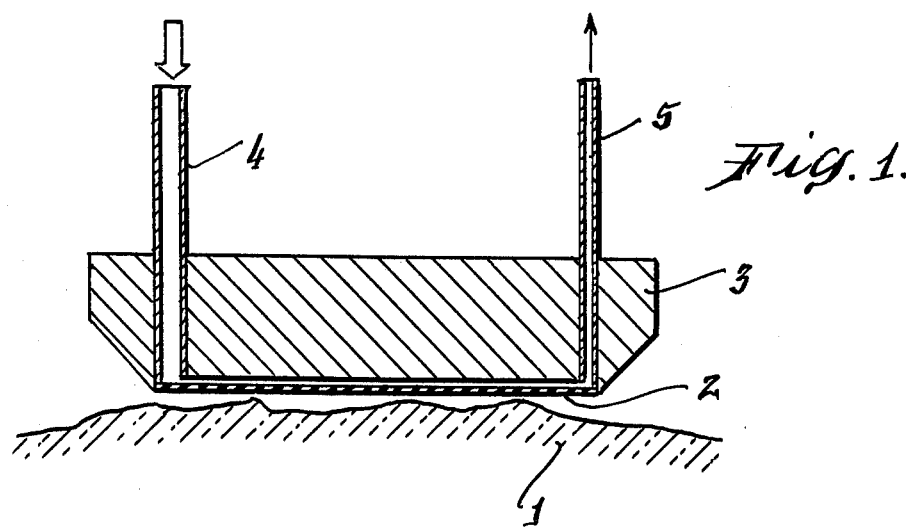
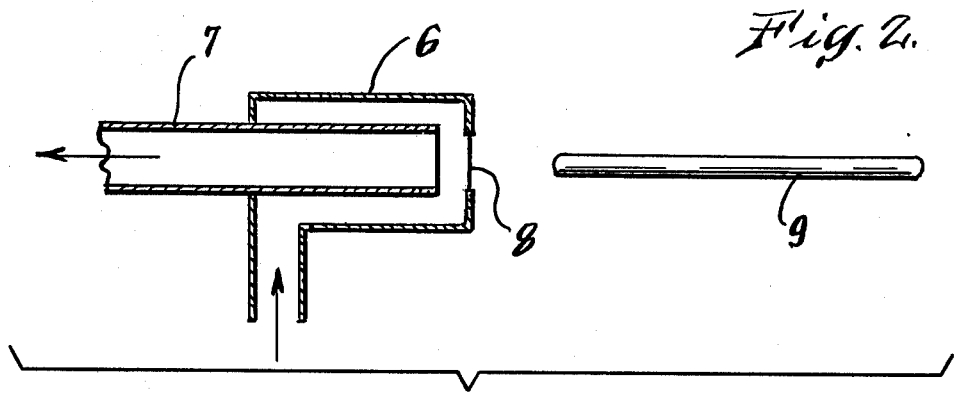
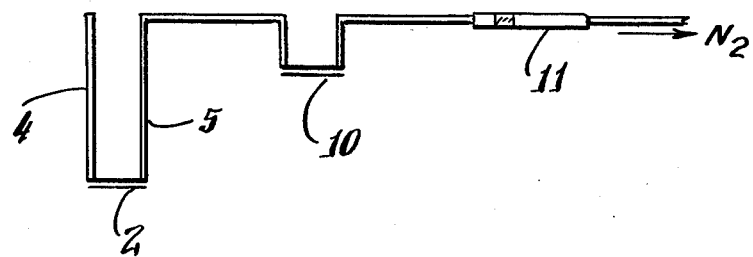

INPUT HEAD OF A MEASURING OR IDENTIFICATION SYSTEM FOR CHEMICAL AGENTS

TECHNICAL FIELD

The invention relates to an input head in accordance with the class defined in claim 1, that is, to an input head of a measuring or detection system for chemical agents for detecting these agents, with a heated membrane, which is exposed directly to the agents which dissolve selectively in the membrane, diffuse through it and emerge in vapor form on the other side, the membrane optionally being backwashed with a carrier gas in order to conduct the agents detected to the system.

STATE OF THE ART

Such an input head has become known through the paper by G. E. Spangler, Internat. Laboratory July/August 1975, pages 24–33 (Section 3 b). It is used in a single stage or a multistage version as an enrichment and inlet system for gaseous samples (such as air samples in monitoring the environment) in gas chromatography or as an interface for the coupling between gas chromatographs and mass spectrometers.

This input head is so constructed, that its application is limited to samples present in gaseous form.

There are however areas of applications, in which this prerequisite is not fulfilled, that is, in which particularly liquid, organic substances are present directly or in aqueous solution.

The German Auslegeschrift No. 2,022,958 describes an input head of a measuring or identification system for chemical agents for detecting these agents, with a heated membrane, which is exposed directly to the agents which dissolve selectively in the membrane, diffuse through it and emerge in vapor form on the other side, and which is backwashed with a carrier gas in order to conduct the agents detected to the system. The organic agents are present exclusively in aqueous solution, that is, the corresponding contaminated liquid is passed over the membrane. In this particular process, the membrane can be self-supporting or it may consist of film of material which is supported on a porous, vitreous support (column 2, lines 20 to 24 of the German Auslegeschrift).

Such a membrane is however not suitable for direct contact with a contaminated solid surface. In the case of a self-supporting embodiment, the membrane would break on contact. In the embodiment, in which the membrane is supported on a porous, vitreous carrier, the supported membrane layer would be shifted and torn.

The known membrane is rigid, inadequately elastic and therefore not sufficiently durable. For this reason, it has been possible until now—in spite of great efforts to the contrary—to determine the agents, which are on the solid surface, only indirectly by converting them into the gaseous phase, for example, by the action of heat. A direct contact of the membrane with the solid surface has not been regarded possible until now.

In one of these areas of application, the input head is used as a detection probe of a mobile detection system, which has the task of detecting dangerous chemicals which contaminate the country, especially of detecting those substances on surfaces of all kinds which, like some warfare agents for example, develop a poisonous effect on contact with the skin.

A further area of application is the usual routine inlet system for gas chromatography (GC) and for the combination of gas chromatograph and mass spectrometer (GC/MS coupling), both important instrumental methods for environmental and trace analysis.

The first-mentioned area of application starts out from the possibility that, as a result of environmental catastrophies or the use of persistent chemical warfare agents, unprotected people will not be able to enter larger areas of the country.

In order to evaluate the extent of such contamination of the country by chemical agents and to be able to decide on concerted protective and defensive measures, numerous qualitative and semiquantitative analyses are required, which can be carried out largely automatically by known procedures and within a short time from a protected detecting vehicle.

For this purpose, a detection probe must be brought actively, and at short intervals of time and space, to the soil or to the surface in question, in order to convey gaseous samples in rapid sequence over a sample line to a suitable detector. In so doing, it must be possible to transfer the substance to be detected in the gaseous phase, largely without decomposition.

Because a high frequency of individual measurements is to be attained, a measurement signal must decline again rapidly; there must not be a memory effect of any importance.

The required sensitivity of the detection system depends on the percutaneous toxicity of the contact poison to be detected; in the case of highly toxic substances, it must be possible to detect coating densities of the order of milligrams per square meter of nonabsorbing surface.

If vaporizable substances are detected on the ground or on a surface by a mobile detection system, but were not identified free of doubt, it becomes necessary to take samples and store them for later examination in an analytical laboratory. The sample size must be sufficient to make possible the identification or structure clarification of the unknown substance.

Previous considerations of the detection probe for chemical contamination of the ground started out from the assumption that the persistent pollutant present would have to be transferred into the gas phase by means of an infrared heater, in order then to be conveyed as a contaminated stream of air through a heated sample line, several millimeters wide, to a detector, which is in the interior of the vehicle.

This arrangement for carrying out the measurements has a series of disadvantages. The main criterion of danger, namely direct contact of skin with the contaminated surface, is inadequately taken into account. Test values, obtained by heating the ground or a surface and vaporizing the pollutant from some distance by means of an IR heater, can be correlated only vaguely with the danger of contact.

The quality of the "surface of the ground" is not defined. To a large extent, it depends on the ground cover and on the effects of the weather, such as vegetation, road surfacing and type of soil. Accordingly, controlled heating above the surface temperature is impossible. On the one hand, heating stays of several minutes are required, in order to attain an adequate vapor pressure in the case of pollutants with a low vapor pressure; on the other, intensive IR radiation, after drying out the vegetation, unavoidably forms interfering pyrolysis products by scorching or even igniting the surface, so that the substance wanted can no longer be detected or the detection system is induced to give a wrong reading.

Contaminated snow would have to be melted first of all and the water formed would have to be evaporated, before there is an adequate increase in temperature.

The air throughput of the previous IR heater/sample line system is of the order of a few liters per minute. Because of the high dilution of the vaporized pollutant, which in any case is present only in trace amounts, this means that all measurements must be carried out in the region of the limit of detection of the detector and that the results obtained are correspondingly uncertain. Even when the coverage density is relatively high, the pollutant concentration in the sample line, and therefore also the signal to noise ratio in very sensitive detectors remains unfavorably small.

Efficient sampling by means of absorption tubes is not possible. Rather, one is dependent on sampling soil, plants or water.

IR heaters and sample lines are afflicted with a memory effect, which originates from the relatively large contaminatable surfaces of the measuring equipment and which is gradually increased by contamination of these surfaces. Materials of low volatility can contaminate the system for hours. The consequent rate of detection, measured by the requirements which may be derived from the application purpose, cannot be accepted.

The power generator, carried along to cover the heating current requirements of several kilowatts for IR heater and sample line, not only is an additional consumer of fuel but also an annoying source of noise; because of its considerable weight, it also affects the driving properties and possibly the ability to float of the detection vehicle.

As mentioned at the beginning, there is a different application in the area of laboratory instrumental trace analysis routines. The detection system here is not actively brought via the detection probe to the immobile sample in question, for example, the point on the ground; rather the reverse, the mobile samples are brought to an immobile GC or GC/MS detection system operated in the laboratory.

The fixed, installed inlet system functions here as a mediator between sample and detection system, similar to the moveable detection probe.

In gas chromatography and coupled GC/MS the sample is usually injected through the so-called injector by drawing up a small volume of liquid, e.g. one microliter of a diluted sample solution, into an injection syringe, piercing a rubber septum with the injection needle and spraying the sample solution into the head of the heated column, through which carrier gas is flowing. Here the sample evaporates and the separation process commences.

The disadvantage of this generally employed sample inlet method lies therein that the sample must be present as an actual liquid or as a solution in an organic solvent, and moreover in an amount, which permits the injection needle to be dipped into the liquid for the filling of the injection syringe.

If however a slight amount of substance to be detected is present in a material sample, for example,
finely divided in a soil sample,
as a thin film or in small droplets on a solid, water or snow surface,
as a volatile component of a paint or of a different thin layer, in which substances, capable of diffusing, are dissolved or on which such substances are absorbed, like plasticizers in plastics,
dissolved or suspended in water or aqueous sludges, an extraction step with an organic solvent must be carried out before the sample is injected. This sample preparation step is time consuming and work intensive. It can however also lead to considerable losses of substance, namely when concentrating relatively volatile substances.

DESCRIPTION OF THE INVENTION

It is an object of the invention to develop the above-described input head in such a manner, that it can be employed more advantageously than previously known solutions in the aforementioned areas of application, that is, to develop a detection probe or a sample inlet system, with the help of which diffusible organic compounds, for example, warfare agents, can be detected, rapidly and with sufficient sensitivity, qualitatively and semiquantitatively, that is, detected and identified on surfaces and in surface layers, in mobile operations and in the laboratory.

This objective is accomplished inventively by virtue of the fact that the membrane is so constructed, that it is as thin as possible and yet sufficiently stable mechanically, so that it can be brought as a contact membrane into direct contact with contaminated solid surfaces, and that the membrane in turn is connected with a sample line, which is also heated and which feeds the sample by means of the carrier gas directly to the detector of the measuring and detection system or which functions as a gas chromatography column, or that the contact membrane is fashioned as the first step of a known membrane separator, for example, a one-step or multi-step Llewellyn membrane separator as a direct inlet system into the high vacuum of a mass spectrometer.

As detector, a mass spectrometer or a different detector, commonly used in gas chromatography, may be employed. A test capillary is also suitable as a detector.

A sorption tube for sampling may be connected to the sample line. The membrane and sample line temperature is in each case advantageously adjusted to the gas chromatographic behavior of the expected substance. The sample line advantageously consists of a chemically inert material, such as, for example, quartz or pure nickel. It may be an uncoated capillary, a coated capillary or a packed or micropacked chromatographic column.

When the contact membrane functions as a direct inlet system into the high vacuum of a mass spectrometer, that is, if no carrier gas is used, an evacuated gas sampling volume is preferably connected in series after the one-step or multi-step membrane separator.

The contact membrane can advantageously be flushed from the outside by a hot inert gas, which maintains the contact membrane at the desired temperature, prevents penetration by undesirable interfering gases, such as oxygen and water vapor, and decreases the memory effect. The contact membrane may be protected by a second, thin, easily exchangeable contact membrane.

SHORT DESCRIPTION OF THE DRAWINGS

The invention is illustrated in greater detail by means of the examples of the operation described in the drawing:

FIG. 1 shows a schematic representation of the inventive input head.

FIG. 2 shows a schematic representation of an inventive GC inlet system.

FIG. 3 shows a schematic representation of a sampling device.

DESCRIPTION OF THE BEST EMBODIMENTS OF THE INVENTION

In FIG. 1, a sample of a chemical agent or of a surface contaminated with a chemical agent is labeled 1. In direct contact with this is a membrane 2, which is mounted on a heated metal block 3. For back-flushing the membrane with a carrier gas, for example, nitrogen, a carrier gas supply line 4 is provided, into which the carrier gas is introduced in the direction of the arrow.

Furthermore, a heated capillary 5 is provided, which can function as a sample line to a detector (not shown) of the detection system, for example, a mass spectrometer (in the direction of the arrow) or which, when used as a GC inlet system, can function as a gas chromatographic column.

The membrane 2 is constructed as thin as possible and is nevertheless sufficiently stable mechanically, so that it can be brought without damage into direct contact with the chemical agents. The agents contacted dissolve selectively in the membrane, diffuse through it and emerge on the other side in vapor form, where they are carried along by the stream of carrier gas and then evaluated further.

The capillary consists advisably of a chemically inert material, for example, quartz or pure nickel, in order to exclude any effect on the agents detected.

The membrane advisably has a chemically inert fabric, which can be stressed thermally and chemically corresponding to the intended application and which is thinly coated uniformly and without gaps with a polymerized paste. The fabric preferably is a 50-200 micrometer thick metal fabric, preferably a braided nickel fabric. The paste advisably is a dimethylsilicone paste.

After the polymerization, the so-treated membrane is subjected to a conditioning process at elevated temperatures.

An essential feature of the arrangement shown in the small surface area of a capillary as well as the high rate of flow and the appropriate temperature of the membrane and the capillary, which is adjusted in each case to the gas-chromatographic behavior of the substance expected.

For use as a soil testing probe for warfare agents, the capillary advisably is a heated nickel capillary, up to 4 m long.

For this purpose, it is advisable to use flame photometer detectors, which simultaneously indicate phosphorus and sulfur, or a microprocessor-controlled mass spectrometer.

The use of the inventive input head as a sample inlet system for gas chromatography and for the combination of gas chromatography and mass spectrometry (coupled GC/MS) is described by means of FIG. 2. Gas chromatography (GC) enables mixtures to be separated and individual components to be identified, provided that they can be transferred without decomposition to the gaseous phase. Essentially, gas chromatographs consist of a sample injector with a heated injector housing 6, which has an inlet 8 for a carrier gas, a chromatographic column 7, through which the carrier gas is flowing, and a detector, which is not shown and which is more or less selective or substance specific, for example, a phosphorus detector or a mass spectrometer (MS).

In the known case, the sample is injected by drawing up a small volume of liquid, for example, 1 $\mu$l of a diluted sample solution into an injection syringe, pushing the injection needle through a 3-4 mm thick rubber septum on the front side of the injector housing and spraying the sample liquid into the opening of the heated chromatographic column, where the sample evaporates and the separation process commences.

The advantage of this generally used sample inlet method lies in the good reproducibility in quantitative analyses; in this procedure however, the operator is expected to have experience and skill.

The disadvantage is that the sample must be present as an actual liquid or as a solution in an organic solvent, and moreover in an amount which permits the injection needle to be dipped, so that the injection syringe can be filled, water being excluded as a solvent.

If there is only a slight amount of a substance to be investigated in a contaminated sample of material, for example, finely divided in a soil sample or as a thin film on a surface, or if the sample is an aqueous solution, the substance must be enriched or extracted with a solvent before a sample of it can be injected.

This sample preparation step is time-consuming and mostly leads to large losses of substance, namely when concentrating solutions of relatively volatile substances.

In the inventive sample inlet system, shown in FIG. 2, the septum of the usual sample injector 6 is replaced by a thin, appropriately heated membrane 8, which is back-flushed with carrier gas. The contaminated sample of material in question is briefly brought into direct contact with the membrane. Any diffusible contaminants present dissolve in the membrane surface, diffuse through the membrane and, after emerging from the reverse side of the membrane, are transported by the carrier gas directly to the chromatographic column 7. A previous solvent extraction is unnecessary.

If the sample is available in a larger amount in the form of a liquid, it is, for example, possible to wet a glass rod 9 with it, which is then contacted with the membrane, an extremely simple process in comparison to an injection with a syringe.

The membrane sample inlet system shown is particularly suitable for coupling with a mass spectrometer, for carrying out rapid qualitative and semi-quantitative survey analyses.

The membrane may also be mounted directly on a mass spectrometer, in order to bring about the direct admission of the sample, that is, the admission without a vacuum lock and without a prior gas chromatographic separation, into the high vacuum of the mass spectrometer. This arrangement is advisable in cases in which a particularly high detection sensitivity is required and, on the basis of prior knowledge, there is already some suspicion of the qualitative composition of the sample.

The chromatographic column 7 may be a packed column; preferably, it is a capillary column.

If unknown materials or materials, which cannot be identified unambiguously, appear when using the detection probe, samples must be taken which later must be analyzed in an analytical laboratory.

A very simple possibility for sampling with a detection probe of FIG. 1 is shown in FIG. 3. This can be realized without any additional mechanical device by combining the capillary sample line 5 with a small collection tube 10. Until now, these samples were taken by means of mechanically operated sampling tools.

The material, picked up by the membrane 2, is passed in gaseous form through capillary 5 to a detector 10, which requires only a portion of the material for the detection.

The remaining portion of the material which flows past, for example, an inlet membrane of a mass spectrometer, is fed by means of a carrier gas or supported by a suction pump to a small tube 11 of the type, which is in common use in many variations in environmental analysis and which is filled with an absorbing material, for example, Tenax-GC.

If the tube is suitably constructed, the adsorbate can be eluted once again.

The advantages of this version of sampling are:

Since samples must be taken in any case in the detection process, an additional sampling device, which is technically expensive and therefore susceptible to breakdown and costly, is unnecessary when soil samples are to be investigated.

The actual surface contamination of interest is selectively detected.

A considerable gain in time is achieved.

Already when sampling, the sample is separated from carrier material such as wet soil, plant material, etc., and this makes the evaluation in the laboratory significantly simpler and shorter: rapid elution of even slight amounts of warfare agents is possible.

The sample is more durable, because it was separated from the active surfaces and is present in relatively high purity and in relatively large amounts.

Individual fractions of multicomponent mixtures can be collected separately and stored. As a result, the later laboratory analysis is also facilitated.

The individual sample has small dimensions, perhaps like those of a small carrier capillary.

The detection probe itself supplies relatively high concentrations even of slight absolute amounts of warfare agents; As a result, good absorption yields are achieved.

Additional energy is not required for a mechanism moved by an electric motor.

INDUSTRIAL USABILITY

Through the invention, the following advantages are achieved in the first-mentioned area of application as a mobile ground detection probe:

The measurement equipment conforms to the needs of the essential moment of danger, the immediate contact of skin with the contaminated surface, insofar as here as there, a membrane or skin absorbs the harmful substance by contact, the flowing medium of carrier gas or body fluid takes over the transport to a place at which the harmful material develops its effect as a detector signal or symptom. The concept therefore makes possible a more realistic, quantitative estimate of the danger.

The high rate of flow in the capillary means rapid sample transport over several meters and therefore a short response time of the detection system.

A memory effect is not observed. The sample line is effectively protected by the membrane from contamination. If suitable membrane and sample line temperatures are selected, even materials of low volatility (with vapor pressures less than $10^3$m bar at 20° C.) can be detected repeatedly within one minute.

As a result of keeping the flow-through volume small at a few milliliters per minute, high concentrations of harmful materials, which originated from traces and have reached the carrier gas practically instantaneously through the membrane, can be produced and recorded by the detector with a correspondingly advantageous ratio of signal intensity to noise.

Overheating of surfaces and therefore pyrolytic disturbances of the measurements are excluded.

Aqueous samples, ice and snow can also be investigated roughly for harmful materials by the rapid procedure, a liquid-solid extraction, with enrichment of the organic components taking place in the hydrophobic silicone membrane.

The detection stoppage amounts only to a few seconds.

The energy of ca. 100 watt required can be covered by the generator of the detection vehicle.

The arrangement permits the development of the sample line into a gas chromatographic column by coating it with a stationary phase. If finally a mass spectrometer is used as a universal detector, a mobile GC/MS system results, which combines in a known advantageous manner the GC separation capability with the sensitivity and variable specificity of the mass spectrometer. The parallel operation of coated and uncoated sample lines for alternative rapid detection or slower identification can be realized. In the latter case, the retention times of the GC separation must be taken into account.

The sampling for later laboratory analysis can conveniently be carried out by means of the sorption tube, through which the carrier gas, containing the harmful material is flowing. By so doing, a stable substance sample, optionally prepurified by gas chromatography, is obtained in an abundant amount.

The following advantages are realized in the second-mentioned area of application—the inlet system for a GC:

For a large number of qualitative and semiquantitative routine and survey analyses, occurring in the GC/MS laboratory, the sample admission is simplified considerably without loss of resolution and sensitivity.

Liquid samples, even aqueous solutions or suspensions, can conveniently be metered out for a rapid survey analysis by wetting a glass rod, which is then contacted with the membrane.

The method can easily be automated.

The quantitative reproducibility is adquate if the conditions are adjusted to the particular problems of the analysis.

In examinations of surfaces for GC-detectible materials, the sample preparation time is reduced to a fraction because of the elimination of the otherwise necessary extraction step, that is, several times as many samples can be handled in the same time. It is only necessary to bring the surface in question up to the contact membrane.

Highly volatile polar solvents such as methanol, which are frequently used in GC/MS analyses because of their low molecular weight, are discriminated against in favor of less polar dissolved materials. In the case of a moderately heated contact membrane, the solvent is removed almost completely before it can enter the chromatographic column. The dissolved material however is enriched relatively as it is absorbed by the membrane and finally is mobilized by a temperature program in the direction of the chromatographic column.

We claim:

1. An input head for a system for actively detecting the presence of chemical agents, said input head comprising:
   a thin membrane adapted to be brought into direct contact with a solid surface containing chemical agents, said membrane being formed from a mechanically stable material which when brought into contact with said solid surface causes said chemical agents to be detected to selectively dissolve and to diffuse through said membrane and exit therefrom in a vaporized state,
   said membrane including a chemically inert fabric which adequately withstands thermal stresses and mechanical stresses resulting from direct contact with the solid surface, said fabric being thinly and uniformly coated without gaps with a polymerizable paste,
   means for directly heating said thin membrane,
   means for supplying a carrier gas proximate to the portion of said thin membrane through which said chemical agents exit in said vaporized state for transporting said vaporized chemical agents diffusing through said thin membrane, and
   a sample line in fluid communication with said carrier gas for receiving said carrier gas and said vaporized chemical agents being transported therewith.

2. The input head as claimed in claim 1 wherein said sample line is located proximate to said means for heating said membrane such that said sample line is also heated by said means for heating said membrane.

3. The input head as claimed in claim 1 wherein said sample line has an outlet coupled to means for detecting said chemical agents.

4. The input head as claimed in claim 3 wherein said means for detecting is a mass spectrometer.

5. The input head as claimed in claim 3 wherein said means for detecting is a gas chromatography detector.

6. The input head as claimed in claim 3 wherein said means for detecting is a test capillary.

7. Input head according to claim 1 further including means for connecting said sample line to an adsorption tube (11) for sampling.

8. Input head according to claim 1 including means for adjusting the temperature of said membrane and said sample line to the gas chromatographic behavior of the chemical agent to be detected.

9. Input head according to claim 1 wherein said sample line (5) is formed from a chemically inert material.

10. Input head according to claim 9 wherein said chemically inert material is quartz.

11. The input head as claimed in claim 9 wherein said chemically inert material is pure nickel.

12. Input head according to claim 1 wherein the sample line is an uncoated capillary (5).

13. Input head according to claim 1 wherein the sample line is a coated capillary column.

14. Input head according to claim 1 wherein the sample line is a packed chromatographic column.

15. Input head according to claim 1 wherein said input head is adapted to be used as a gas chromatographic inlet system.

16. An input head for a system for actively detecting the presence of chemical agents, said input head comprising:
   a thin membrane adapted to be brought into direct contact with a solid surface containing chemical agents, said membrane being formed from a mechanically stable material which when brought into contact with said solid surface causes said chemical agents to selectively dissolve and to diffuse through said membrane and exit therefrom in a vaporized state,
   said membrane including a chemically inert fabric which adequately withstands thermal stresses and mechanical stresses resulting from direct contact with the solid surface, said fabric being thinly and uniformly coated without gaps with a polymerizable paste,
   means for directly heating said thin membrane,
   means for coupling said thin membrane to a membrane separator having a high vacuum mass spectrometer, said membrane being a direct inlet into said mass spectrometer.

17. Input head according to claims 1 or 16, wherein said fabric is a metal fabric, 50 to 200 $\mu$m thick.

18. Input head according to claim 17, wherein said metal fabric is a braided nickel fabric.

19. Input head according to claims 1 or 16, wherein said polymerizable paste is a dymethylsilicone paste.

20. Input head according to claims 1 or 16 wherein said input head is adapted to be used as a detection probe for the mobile detection of organic substances, which are present on solid surfaces and within thin layers of substances.

21. Input head according to claims 1 or 16 wherein said fabric is a metal fabric, 50 to 200 $\mu$m thick, and said polymerizable paste is a dymethylsilicone paste.

22. Input head according to claim 21 wherein said metal fabric is a braided nickel fabric.

* * * * *